United States Patent
Kajii

(10) Patent No.: US 7,655,910 B2
(45) Date of Patent: Feb. 2, 2010

(54) APPARATUS FOR GAS CONCENTRATION MEASUREMENT ACCORDING TO GAS CORRELATION METHOD

(75) Inventor: Yoshizumi Kajii, Setagaya-ku (JP)

(73) Assignee: Japan Science and Technology Agency (JP)

( * ) Notice: Subject to any disclaimer, the term of this patent is extended or adjusted under 35 U.S.C. 154(b) by 349 days.

(21) Appl. No.: 11/816,055

(22) PCT Filed: Feb. 13, 2006

(86) PCT No.: PCT/JP2006/302447

§ 371 (c)(1),
(2), (4) Date: Aug. 10, 2007

(87) PCT Pub. No.: WO2006/085646

PCT Pub. Date: Aug. 17, 2006

(65) Prior Publication Data

US 2009/0026374 A1    Jan. 29, 2009

(30) Foreign Application Priority Data

Feb. 14, 2005    (JP) .............................. 2004-036885

(51) Int. Cl.
*G01J 5/02* (2006.01)
(52) U.S. Cl. .................. 250/343; 250/339.13
(58) Field of Classification Search ............ 250/339.01, 250/350

See application file for complete search history.

(56) References Cited

U.S. PATENT DOCUMENTS

| | | | |
|---|---|---|---|
| 3,904,880 | A | 9/1975 | Benz et al. |
| 3,968,367 | A | 7/1976 | Berg |
| 4,236,827 | A | 12/1980 | Horiba et al. |
| 5,036,198 | A | 7/1991 | Spaeth |

(Continued)

FOREIGN PATENT DOCUMENTS

JP    60-149949 A    8/1985

(Continued)

OTHER PUBLICATIONS

International Search Report (ISR) for PCT/JP2006/302447 for Examiner consideration, citing U.S. patents Nos. 1-5 and foreign references Nos. 1-3 listed above, 2006.

(Continued)

*Primary Examiner*—David P Porta
*Assistant Examiner*—Carolyn Igyarto
(74) *Attorney, Agent, or Firm*—Chen Yoshimura LLP

(57) ABSTRACT

A gas concentration measuring apparatus utilizing a gas correlation method capable of measuring concentrations of a plurality of analyte gases simultaneously and at high sensitivity uses an infrared light source (2) such as an infrared semiconductor diode or a quantum cascade semiconductor laser to increase the intensity of collimated infrared light (5) and to lessen infrared light unnecessary for measurement, thereby improving the S/N ratio while achieving a rise in sensitivity. A plurality of analyte gases are simultaneously measured by means of a gas correlation filter comprising a reference gas cell (6a) filled with all of the analyte gases and a plurality of probe gas cells (6b) each individual of which is filled with all such analyte gases other than one of the analyte gases which is of its particular interest.

5 Claims, 9 Drawing Sheets

U.S. PATENT DOCUMENTS

| | | | |
|---|---|---|---|
| 5,585,635 A | | 12/1996 | Graham |
| 5,693,945 A | * | 12/1997 | Akiyama et al. ............ 250/345 |
| 5,900,635 A | * | 5/1999 | Weckstrom ................. 250/345 |
| 6,599,253 B1 | | 7/2003 | Baum et al. |

FOREIGN PATENT DOCUMENTS

| | | |
|---|---|---|
| JP | 2-66428 A | 3/1990 |
| JP | 8-105833 A | 4/1996 |

OTHER PUBLICATIONS

PCT/ISA/237 in PCT/JP2006/302447 and its translation of Section V, 2006.

Jerome Faist et al., "Distributed feedback quantum cascade lasers" in "Applied Physics Letters", vol. 70, No. 20, May 19, 1997, pp. 2670-2672 Cited on p. 5 of the as-filed translation of the specification.

C. Domoto et al., "Intersubband electroluminescence using X-Γ carrier injection in a GaAs/AlAs superlattice" in "Applied Physics Letters", vol. 77, No. 6, Aug. 7, 2000, pp. 848-850 Cited on p. 5 of the as-filed translation of the specification.

Yoshito Nishijima, "PbSnTe double-heterostructure lasers and PbEuTe double-heterostructure lasers by hot-wall epitaxy" in Journal of Applied Physics, vol. 65, No. 3, Feb. 1, 1989, pp. 935-940 Cited on p. 5 of the as-filed translation of the specification.

J. I. Malin et al., "Optically Pumped Mid-IR Type II Quantum Well Lasers" in "SPIE", vol. 2682, 1996, pp. 257-266 Cited on p. 5 of the as-filed translation of the specification.

Translation of PCT/ISA/237 in PCT/JP2006/302447 and its transmittal form of IB338 and IB373, 2006.

Nippon Thermo Co. Ltd., http://www.thermo.co.jp/tameninaru1-6.html, 11 pages, Jun. 19, 2003, printed from the Internet on Jun. 15, 2007. Cited on page 5 of the as-filed translation of the specification. A concise explanation of relevance is provided on pp. 1-2 of the originally filed specification.

J. I. Malin et al., "Optically Pumped Mid-IR Type ll Quantum Well Lasers" in "SPIE", vol. 2682, 1996, pp. 257-266 cited on p. 5 of the as-filed translation of the specification.

Translation of PCT/ISA/237 in PCT/JP2006/302447 and its transmittal form of IB338 and IB373.

* cited by examiner (a)

Reference Light (b)

Probe Light B (c)

Probe Light A (d)

(a)

(b)

(c)

APPARATUS FOR GAS CONCENTRATION MEASUREMENT ACCORDING TO GAS CORRELATION METHOD

TECHNICAL FIELD

The present invention relates to an apparatus for gas concentration measurement according to a gas correlation method whereby concentrations of a plurality of trace substances in a gas can be detected at high sensitivity and simultaneously.

BACKGROUND ART

The high-sensitivity detection of trace substances in a gas is becoming extremely important in diverse fields such as those of pollution prevention, specimen analysis, environmental monitoring and earth science. As one of conventional high-sensitivity detection apparatuses for trace substances in a gas, there is an apparatus utilizing a gas correlation method which has widely been used such as for measuring CO concentrations in exhaust gases of incinerators. The gas correlation method is a method of detecting gaseous trace substances which is prescribed by the United States Environmental Protection Agency (U.S. EPA), and is a sort of non-dispersive infrared absorption system. This method, which allows detection with high sensitivity as its effect of interference by a gaseous substance other than trace substances to be measured is limited and which is low in its apparatus cost, has widely been used in general.

Mention is now made of the conventional apparatus and concentration measuring method, which utilize the gas correlation method.

FIG. 8 is a diagrammatic cross-sectional view illustrating the makeup of a conventional apparatus for concentration measurement according to the gas correlation method (see Nonpatent Reference 1.). The apparatus 50 for concentration measurement according to the gas correlation method comprises: an infrared light source 51 of thermal radiation type; an optical system (collimator) 52 for collimating infrared light 51a generated by the infrared light source 51; a gas correlation filter 53 through which collimated infrared light 51a passes; a bandpass filter 54 for limiting a passband of the infrared light 51a passing through the gas correlation filter 53; a multi-reflection sample gas cell 55 in which a gas to be measured 55a is introduced or charged and through which infrared light 51a that has passed through the band-pass filter 54 passes; and an infrared detector 56 for measuring an intensity of infrared light 51a passing through the multi-reflection sample gas cell 55.

The gas correlation filter 53 consists of a gas cell 53a filled with an analyte gas at high concentration and a gas cell 53b filled with a gas not absorbing the infrared light, e. g., $N_2$ gas. The gas cell 53a is used to form reference light excluding absorption spectral components of an analyte gas from infrared light 51a while the gas cell 53b is used to form probe light similar in level of light dispersion such as of Rayleigh scattering to the reference light. These gas cells are rotated about the central axis 53c of the gas correlation filter 53 to make such infrared light 51a successively incident on these two gas cells.

By selecting a passband of the bandpass filter 54 to be wider than and close as much as possible to an infrared absorption band of an analyte gas, it is possible to decrease an interference effect by a gas other than the analyte gas and to measure its concentration at high sensitivity. Here, the interference effect is meant to refer to an adverse effect on a measured value of the concentration of a analyte gas by that of a gas other than the analyte gas in the presence of skirt portions of the absorption spectrum of that other gas on those of the passband of the bandpass filter so as to cause infrared light of the passband of the bandpass filter to be absorbed by that other gas.

FIG. 9 carries charts illustrating principles of the conventional concentration measurements according to the gas correlation method. FIG. 9 (a) shows a spectrum formed by infrared light 51a passing through the bandpass filter 54, namely that of incident reference light that is incident on the multi-reflection sample gas cell 55. Numeral 61 designates a spectral defect caused by the absorption by an analyte gas filled in the gas cell 53a at high concentration while numeral 61a designates a spectral shape made up with the bandpass filter 54.

FIG. 9(b) shows a spectrum formed by infrared light 51a passing through the bandpass filter 54, namely that of incident probe light that is incident on the multi-reflection sample gas cell 55. Since the gas filled in the gas cell 53b absorbs no infrared light, it is shown that there is no such spectral defect.

FIG. 9(c) shows the spectrum of reference light detected by the infrared detector 56, which is shown damped by a loss in the optical system due to contaminations of mirrors in the multi-reflection sample gas cell 55 and their deviations of optical axes, namely by that other than an absorption loss by an analyte gas in the gas to be measured 55a.

FIG. 9(d) shows the spectrum of probe light detected by the infrared detector 56, which is shown damped not only by a loss other than an absorption loss of an analyte but also by such an absorption loss of the analyte in the gas to be measured 55a. Numeral 62 indicates a damping by absorption of the analyte gas. The frequency domain in which the absorption occurs corresponds to that in which the spectral defect 61 in FIG. 9(a) occurs.

Since the loss in the optical system due to contaminations of the collimator 52, gas correlation filter 53 and bandpass filter 54 and their deviations of optical axes has no dependence on a frequency of infrared light and cause incident probe and reference light intensities $I_{p0}$ and $I_{r0}$ to be damped at an identical loss factor, ratio of the incident probe light intensity to the incident reference light intensity: $I_{p0}/I_{r0}$ is constant against their changes and also is constant against changes in output light intensity of the infrared light source 51. Here, since the incident probe light intensity $I_{p0}$ is proportional to an area of hatched portion in (b) and the incident reference light intensity $I_{r0}$ is proportional to an area of hatched portions in FIG. 9(a), $I_{p0}/I_{r0}$ represents a ratio in area of the hatched portion in FIG. 9(b) to the hatched portions in FIG. 9(a), that is a spectral area ratio.

Likewise, since the loss of the optical system based on contaminations of such as mirrors of the multi-reflection sample gas cell 55 and their deviations of optical axes in the optical system, namely the loss other than of absorption by an analyte gas damps incident reference and probe light intensities $I_{r0}$ and $I_{p0}$ at an identical loss factor, ratio: $I_p/I_r$, of probe light intensity $I_p$ to reference light intensity $I_r$, where they are detected by the infrared detector 56 is constant against their variations. Here, the probe light intensity $I_p$ detected by the infrared detector 56 is proportional to an area of the hatched portion in FIG. 9(d) and the reference light intensity $I_r$ is proportional to an area of the hatched portions in FIG. 9(c). Thus $I_p/I_r$ is a ratio in area of the hatched portion in FIG. 9(d) to the hatched portions in FIG. 9(c), that is a spectral area ratio.

The reference light has not the absorption spectral component of an analyte gas and its intensity will in no case be damped by its absorption by the analyte gas in the gas to be measured 55a. Therefore, loss γ other than loss of absorption by the analyte gas in the multi-reflection sample gas cell 55 can be found from the ratio: $I_r/I_{r0}$, of the reference light intensity detected at the infrared detector 56 to the incident reference intensity as follows:

[Formula 1]

$$\gamma = I_r/I_{r0} \quad (1)$$

The probe light intensity $I_p$ detected at the infrared detector 56 has both the loss γ other than that of absorption by the analyte gas in the multi-reflection sample gas cell 55 and that loss of absorption by the analyte gas. Then, assuming that the degree of absorption by the analyte gas is α, the probe light intensity $I_p$ can be expressed with using γ and the incident probe light intensity $I_{p0}$ by equation (2) below.

[Formula 2]

$$I_p = \gamma I_{p0} e^{-\alpha} \quad (2)$$

Substituting γ in equation (2) with equation (1) gives equation (3) below.

[Formula 3]

$$I_p = (I_r/I_{r0}) I_{p0} e^{-\alpha} \quad (3)$$

Equation (3) can be modified to give equation (4) below.

[Formula 4]

$$I_p/I_r = (I_{p0}/I_{r0}) e^{-\alpha} \quad (4)$$

The equation (4) shows that the degree of absorption can be found from the ratio $I_p/I_r$ of the probe and reference light intensities $I_p$ and $I_r$ detected by the infrared detector 56 and the ratio $I_{p0}/I_{r0}$ of the incident probe and reference light intensities $I_{p0}$ and $I_{r0}$ which can be measured when the apparatus is manufactured. Since as mentioned above $I_{p0}/I_{r0}$ is constant against changes in output light intensity of the infrared light source 51 and changes in loss in the optical system of the collimator 52, the gas correlation filter 53 and the bandpass filter 54 and $I_p/I_r$ is constant against losses other than the loss of absorption by the analyte gas in the multi-reflection sample gas cell 55, a trace substance in a gas can be detected from the degree of absorption α found by this method, without being affected by such changes.

Nonpatent Reference 1: http://www.thermo.co.jp/tameninaru1-6.html

Nonpatent Reference 2: J. Faist, C. Gmachl, F. Capasso, C. Sirtori, D. L. Sivco, N. J. Baillargeon and A. Y. Cho: Appl. Phys. Lett. 70, 2670-2672 (1997)

Nonpatent Reference 3: C. Dmoto, N. Ohtani, K. Kuroyanagi, P. O. Baccaro, H. Takeuchi, M. Nakayama and T. Nishimura, "Intersubband Electroluminescence using X-Γ Carrier Injection in a GaAs/AlAs Superlatice"; Appl. Phys. Lett. 77, 848 (2000)

Nonpatent Reference 4: Y. Nishijima: J. Appl. Phys. 65, pp. 935-940

Nonpatent Reference 5: J. I. Malin, J. R. Meyer, C. L. Felix, J. R. Lindle, L. Goldberg, C. A. Hoffman, F. J. Bartoli, C.-H. Lin, P. C. Chang, S. J. Murry, R. Q. Yang, and S.-S. Pei: SPIE Vol. 2682, pp. 257-261 (1996)

DISCLOSURE OF THE INVENTION

Problems to be Solved by the Invention

With such a gas concentration measuring apparatus of portable type using the gas correlation method in the prior art, however, the measuring sensitivity has its limits in the order of ppm and it is difficult to measure at a sensitivity in the order of ppb. The reasons why it is difficult to effect a measurement in the order of ppb with the conventional apparatus for measuring concentrations of trace substances using the gas correlation method is that since the infrared light source is of thermal radiation type such as an infrared lamp, infrared light emitted radiates in directions of 360°, even if reflecting and collector mirrors are used, collimated infrared light of enough intensity could hardly be obtained and where collimated infrared light of sufficient intensity could by no means be utilized, attempting to raise the measurement sensitivity by making the multi-reflection sample gas cell longer in effective optical length results in damping of the light intensity to an extent that it cannot be detected by a photodetector. Another reason is that since the infrared light source of thermal radiation type emits infrared light of an extremely broad band unnecessary for measurement, infrared light over a rejection band of the bandpass filter comes into the infrared detector and deteriorates its S/N ratio.

While the apparatus of ppm order in measurement sensitivity is sufficient for applications such as detection of a noxious gas in exhaust gases of an incinerator, it is insufficient in measurement sensitivity if used for an application such as the sample analysis, environmental monitoring and earth science. For example, in order to preserve the earth environment, it is required to precisely understand the mechanism in which air pollution occurs from terrestrial points of view and then to take measures to meet the situation. To this end, it is necessary to make a measurement for extremely low concentrations of polluting substances in an area such as the stratosphere or troposphere or a great ocean and then to achieve a sensitivity of detection of at least ppb (a ratio of one-billionth). It is difficult, however, to make a detection of ppb order with the conventional, portable concentration measuring apparatus using the gas correlation method.

In order to learn the mechanism in which air pollution occurs, it is also necessary to measure concentrations of a plurality of analyte gases simultaneously. In an atmospheric state that photochemical reactions occur, reactions of transforming from $NO_2$ to NO and from NO to $NO_2$ may occur in an extremely short period. Then, elucidating the mechanism makes it necessary to know their reaction rates and to measure the momentarily changing concentrations of analyte gases. Since the conventional apparatus of this sort can only measure a single analyte gas at a time, it has then been necessary, for example, to prepare both an apparatus for measuring a $NO_2$ concentration and an apparatus for measuring a NO concentration and separately measure these momentarily changing concentrations with the two units of apparatus; hence the measurement has been far less than expedient.

Thus, there have hitherto been the problems with the conventional portable gas concentration measuring apparatus using the gas correlation method that it is difficult to measure at a sensitivity in the order of ppb and that it is not possible to simultaneously measure concentrations of a plurality of analyte gases in a gaseous mixture.

In view of the problems mentioned above, it is an object of the present invention to provide an apparatus for gas concentration measurement using a gas correlation method whereby concentrations of a plurality of trace substances in a gaseous mixture can be detected at a sensitivity of ppb order and simultaneously.

Means for Solving the Problems

In order to achieve the object mentioned above, there is provided in accordance with the present invention in a first aspect thereof an apparatus for gas concentration measurement according to a gas correlation method, characterized in that it comprises: an infrared light source made of an infrared light emitting diode; a collimator for collimating infrared light generated from the infrared light source; a gas correlation filter on which infrared light collimated by the collimator is incident; a multi-reflection sample gas cell on which infrared light passing through the gas correlation filter is incident and in which a gas to be measured containing a plurality of analyte gases is introduced or charged; and an infrared detector for detecting an intensity of infrared light passing through the multi-reflection sample gas cell, wherein: the infrared light source has an infrared light emission band wider than and close to infrared absorption bands of the analyte gases; the gas correlation filter comprises a reference gas cell and a plurality of probe gas cell corresponding in number to a plurality of the analyte gases; the reference gas cell and the probe gas cells are arranged so that the infrared light collimated as aforesaid passes successively through the reference gas cell and the probe gas cells, respectively; and the reference gas cell is filled with all of the analyte gases while each individual of said probe gas cells is filled with all such analyte gases other than one of the analyte gases which is of its particular interest, whereby concentrations of the said analyte gases contained in the gas to be measured are measured at high sensitivity and simultaneously.

The present invention provides in a second aspect thereof an apparatus for gas concentration measurement according to a gas correlation method, characterized in that it comprises: an infrared light source made of an infrared light emitting diode; a collimator for collimating infrared light generated from the infrared light source; a gas correlation filter on which infrared light collimated by the collimator is incident; a bandpass filter for limiting a band of infrared light passing through the gas correlation filter; a multi-reflection sample gas cell on which infrared light whose band is limited by the bandpass filter is incident and in which a gas to be measured containing a plurality of analyte gases is introduced or charged; and an infrared detector for detecting an intensity of infrared light passing through the multi-reflection sample gas cell, wherein: the infrared light source has an infrared light emission band wider than infrared absorption bands of the analyte gases; the gas correlation filter comprises a reference gas cell and a plurality of probe gas cell corresponding in number to a plurality of the analyte gases; the reference gas cell and the probe gas cells are arranged so that the infrared light collimated as aforesaid passes successively through the reference gas cell and the probe gas cells, respectively; the reference gas cell is filled with all of the analyte gases while each individual of the probe gas cells is filled with all such analyte gases other than one of the analyte gases which is of its particular interest, and the bandpass filter has a passband wider than and close to the infrared absorption bands of the analyte gases, whereby concentrations of the analyte gases contained in the gas to be measured are measured at high sensitivity and simultaneously.

The present invention provides in a third aspect thereof an apparatus for gas concentration measurement according to a gas correlation method, characterized in that it comprises: an infrared light source made of a broadband infrared light emitting semiconductor laser; a collimator for collimating infrared light generated from the infrared light source; a gas correlation filter on which infrared light collimated by the collimator is incident; a multi-reflection sample gas cell on which infrared light passing through the gas correlation filter is incident and in which a gas to be measured containing a plurality of analyte gases is introduced or charged; and an infrared detector for detecting an intensity of infrared light passing through the multi-reflection sample gas cell, wherein: the infrared light source has an infrared light emission band wider than and close to infrared absorption bands of the analyte gases; the gas correlation filter comprises a reference gas cell and a plurality of probe gas cell corresponding in number to a plurality of the analyte gases; the reference gas cell and the probe gas cells are arranged so that the infrared light collimated as aforesaid passes successively through the reference gas cell and the probe gas cells, respectively; and the reference gas cell is filled with all of the analyte gases while each individual of the probe gas cells is filled with all such analyte gases other than one of the analyte gases which is of its particular interest, whereby concentrations of the analyte gases contained in the gas to be measured are measured at high sensitivity and simultaneously.

The present invention provides in a fourth aspect thereof an apparatus for gas concentration measurement according to a gas correlation method, characterized in that it comprises: an infrared light source made of a broadband infrared light emitting semiconductor laser; a collimator for collimating infrared light generated from the infrared light source; a gas correlation filter on which infrared light collimated by the collimator is incident; a bandpass filter for limiting a band of infrared light passing through the gas correlation filter; a multi-reflection sample gas cell on which infrared light whose band is limited by the bandpass filter is incident and in which a gas to be measured containing a plurality of analyte gases is introduced or charged; and an infrared detector for detecting an intensity of infrared light passing through the multi-reflection sample gas cell, wherein: the infrared light source has an infrared light emission band wider than infrared absorption bands of the analyte gases; the gas correlation filter comprises a reference gas cell and a plurality of probe gas cell corresponding in number to a plurality of the analyte gases; the reference gas cell and the probe gas cells are arranged so that the infrared light collimated as aforesaid passes successively through the reference gas cell and the probe gas cells, respectively; the reference gas cell is filled with all of the analyte gases while each individual of the probe gas cells is filled with all such analyte gases other than one of the analyte gases which is of its particular interest, and the bandpass filter has a passband wider than and close to the infrared absorption bands of the analyte gases, whereby concentrations of the analyte gases contained in the gas to be measured are measured at high sensitivity and simultaneously.

The broadband infrared light emitting semiconductor laser is preferably a quantum cascade semiconductor laser having a number of quantum wells adjusted in well width and connected in cascade such that its emitting light has a band wider than and close to the infrared absorption bands of the analyte gases, because an optimal infrared light source can be used depending upon the infrared absorption bands of a plurality of analyte gases.

EFFECTS OF THE INVENTION

According to the apparatus for gas concentration measurement using the gas correlation method, since an infrared light emitting diode or a broadband infrared semiconductor laser is used as the infrared light source and it thus allows in directivity and intensity which increases the effective optical length in the multi-reflection sample gas cell, the detection sensitivity of the apparatus can be made higher. The infrared light emitting diode and broadband infrared semiconductor laser, which do not generate unnecessary infrared emissions as an infrared light source of thermal radiation type, and hence do not deteriorate the S/N ratio, allows raising the detection sensitivity.

The gas correlation filter for use in a gas concentration measuring apparatus according to the present invention comprises a single reference gas cell and a plurality of probe gas cells corresponding to a plurality of analyte gases, respectively. The reference gas cell is filled with all of the analyte gases. The infrared light passing through this gas cell does not contain the absorption spectral components of the analyte gases and can thus be used as reference light for measuring the loss in the optical system. Each individual of the probe gas cells is filled with all such analyte gases other than a particular one of the analyte gases which corresponds to the individual probe gas cell. The infrared light passing through this probe gas cell does not contain the absorption spectral components of such analyte gases other than the particular one of the analyte gases which corresponds to this probe gas cell and can thus be used as probe light for the particular targeted analyte gas. Since the reference gas cell and the probe gas cells are arranged so that the infrared light collimated passes successively through the reference gas cell and probe gas cells, respectively, concentrations of such a plurality of analyte gases can simultaneously be measured with a single unit of the apparatus.

In the apparatus for gas concentration measurement according to the gas correlation method in accordance with the first or the third aspect of the present invention, the infrared light source having an infrared light emission band wider than and close to infrared absorption bands of a plurality of analyte gases is used and it thus eliminates the need for a bandpass filter found necessary in the prior gas correlation method. Hence it can contribute to reducing the apparatus cost.

While trace substances in air which cause air pollution such as, e.g., $N_2O$, $NO_2$, NO, CO, $CH_4$ and $SO_2$ are known, using the apparatus of the present invention makes it possible to measure concentrations of such substances in the ppb order and yet to measure their concentrations simultaneously.

DESCRIPTION OF REFERENCE CHARACTERS

Figure 1:
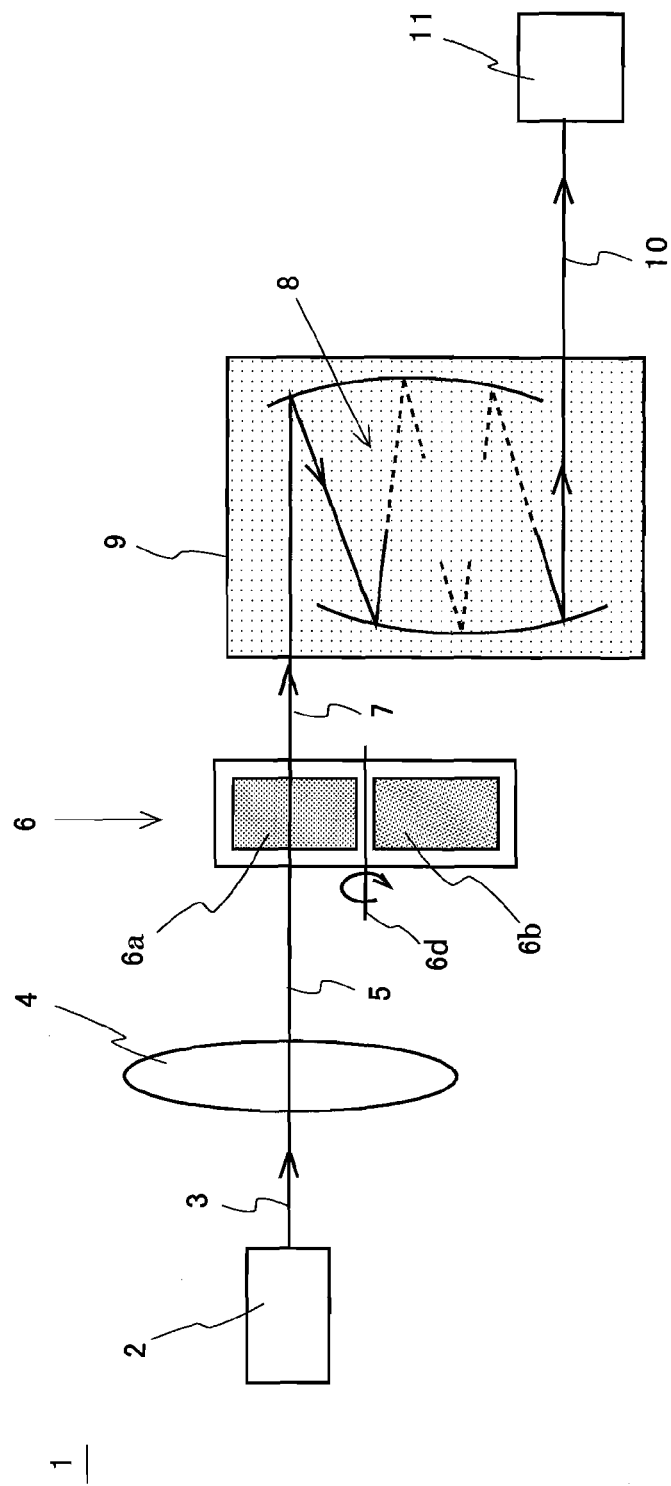
FIG. 1 is a diagram illustrating the makeup of an apparatus for gas concentration measurement according to a gas correlation method which represents a first best form of implementation of the present invention.

1, 20: gas concentration measuring apparatus
2, 21: infrared light source
3, 5, 7, 10: infrared light
4: collimator
6: gas correlation filter
6a: gas cell filled with an analyte gas
6b: gas cell filled with a gas not absorbing the infrared light
8: gas to be measured
9: multi-reflection sample gas cell
11: infrared detector
22: bandpass filter

BEST MODE FOR CARRYING OUT THE INVENTION

Hereinafter, the present invention will be described in detail with reference to certain best forms of implementation thereof illustrated in the drawing figures in which like reference characters are used to designate essentially identical parts.

FIG. 1 is a diagram illustrating the makeup of an apparatus for gas concentration measurement according to a gas correlation method which represents a first best form of implementation of the present invention. In the Figure, the gas concentration measuring apparatus 1 is shown comprising: an infrared light source 2 made up of an infrared light emitting diode or a broadband infrared semiconductor laser; a collimator 4 for collimating infrared light 3 generated from the infrared light source 2; a gas correlation filter 6 on which infrared light 5 collimated by the collimator 4 is incident; a multi-reflection sample gas cell 9 in which a gas to be measured 8 is introduced or charged on which the infrared light 7 that has passed through the gas correlation filter 6 is incident; and an infrared detector 11 for detecting an intensity of infrared light 10 passing through the multi-reflection sample gas cell 9. The infrared light source 2 used is constituted by an infrared light emitting diode or a broadband infrared semiconductor laser which has an infrared light emission band wider than and close to an infrared absorption band of an analyte gas.

The gas correlation filter 6 comprises a reference gas cell 6a filled with all of the analyte gases at high concentrations and a plurality of probe gas cells 6b each individual of which is filled with all such analyte gases other than one of the analyte gases that is of its particular interest, all at high concentration. The probe gas cells 6b that correspond in number to a plurality of the analyte gases are collectively designated by 6b. The gas correlation filter 6 is shown rotating about an axis of rotation 6d so that infrared light 5 passes successively through the gas cell 6a and gas cells 6b. Here, the term "filled at high concentration" is intended to mean "filled with such high concentration that absorption of infrared light 5 by an analyte gas or gases contained in a gas cell reaches 100% and that infrared light passing through one gas cell becomes equal in light dispersion such as Rayleigh scattering to that passing through another".

Since the spectrum of infrared light passing through the reference gas cell 6a filled with all of the analyte gases has its infrared absorption band spectral components for a plurality of analyte gases absorbed by them and has no such infrared absorption band spectral components, the infrared light when passing through the multi-reflection sample gas cell does not incur the loss due to absorption by the analyte gases but incurs only an optical loss of the multi-reflection sample gas cell. Therefore, it can be used as reference light for measuring an absorption loss other than that by a plurality of analyte gases.

On the other hand, the spectrum of infrared light passing through each individual probe gas cell 6b filled with all such analyte gases other than a particular one of the analyte gases which is targeted by the individual probe gas cell has its infrared absorption band spectrum components for these analyte gases absorbed by them and has no such infrared absorption band spectral components. Therefore, the absorption loss which the infrared light when passing through the multi-reflection sample gas cell incurs is only an absorption loss by the analyte gas which is targeted by the particular gas cell.

Figure 8:
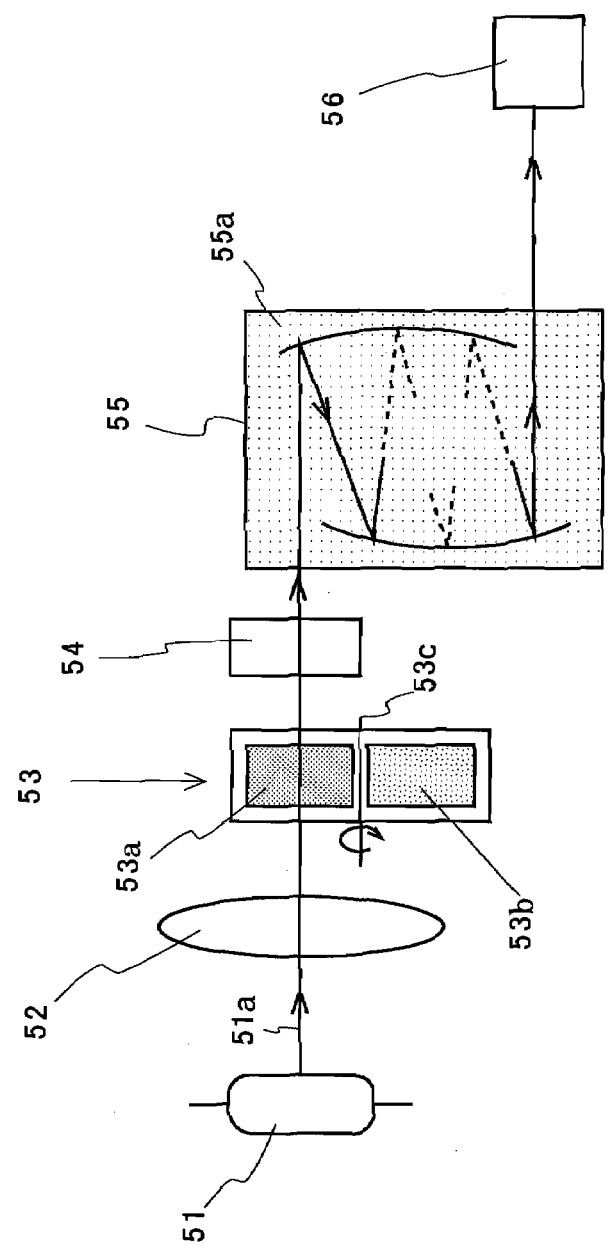
FIG. 8 is a diagram illustrating the makeup the conventional apparatus for gas concentration measurement according to the gas correlation method.
Figure 9:
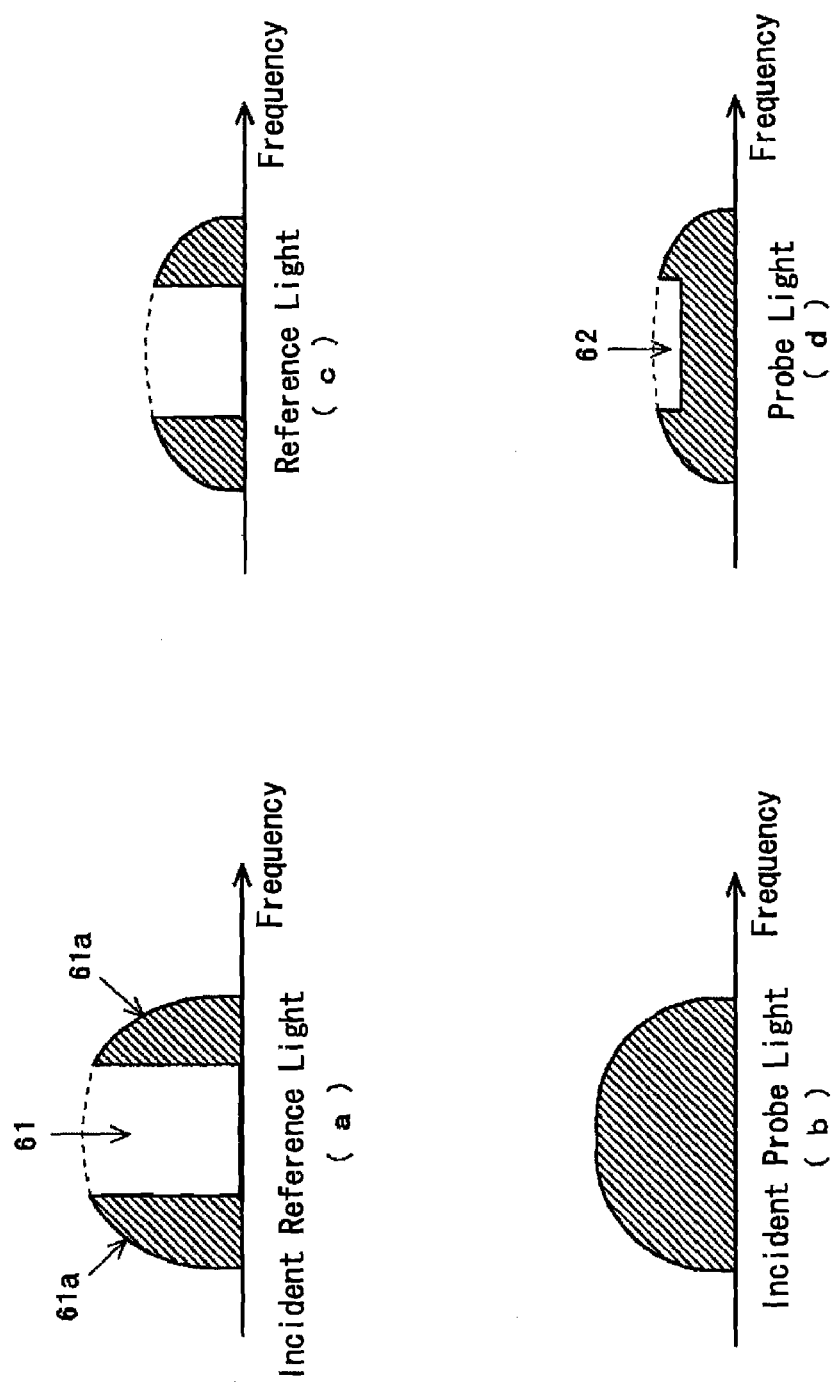
FIG. 9 carries charts illustrating principles of the conventional concentration measurements according to the gas correlation method.

Since the reference gas cell 6a and the probe gas cells 6b are arranged so that the infrared light collimated as aforesaid passes successively through them, respectively, it is possible to measure concentrations of a plurality of analyte gases simultaneously with a single unit of the apparatus. For the multi-reflection sample gas cell 9 and the infrared detector 11 which are like those in the prior art mentioned in FIG. 8, a repeated description is omitted.

Mention is now made of an infrared light emitting diode to be used in connection with an example in which analyte gases are NO and $NO_2$.

Figure 2:
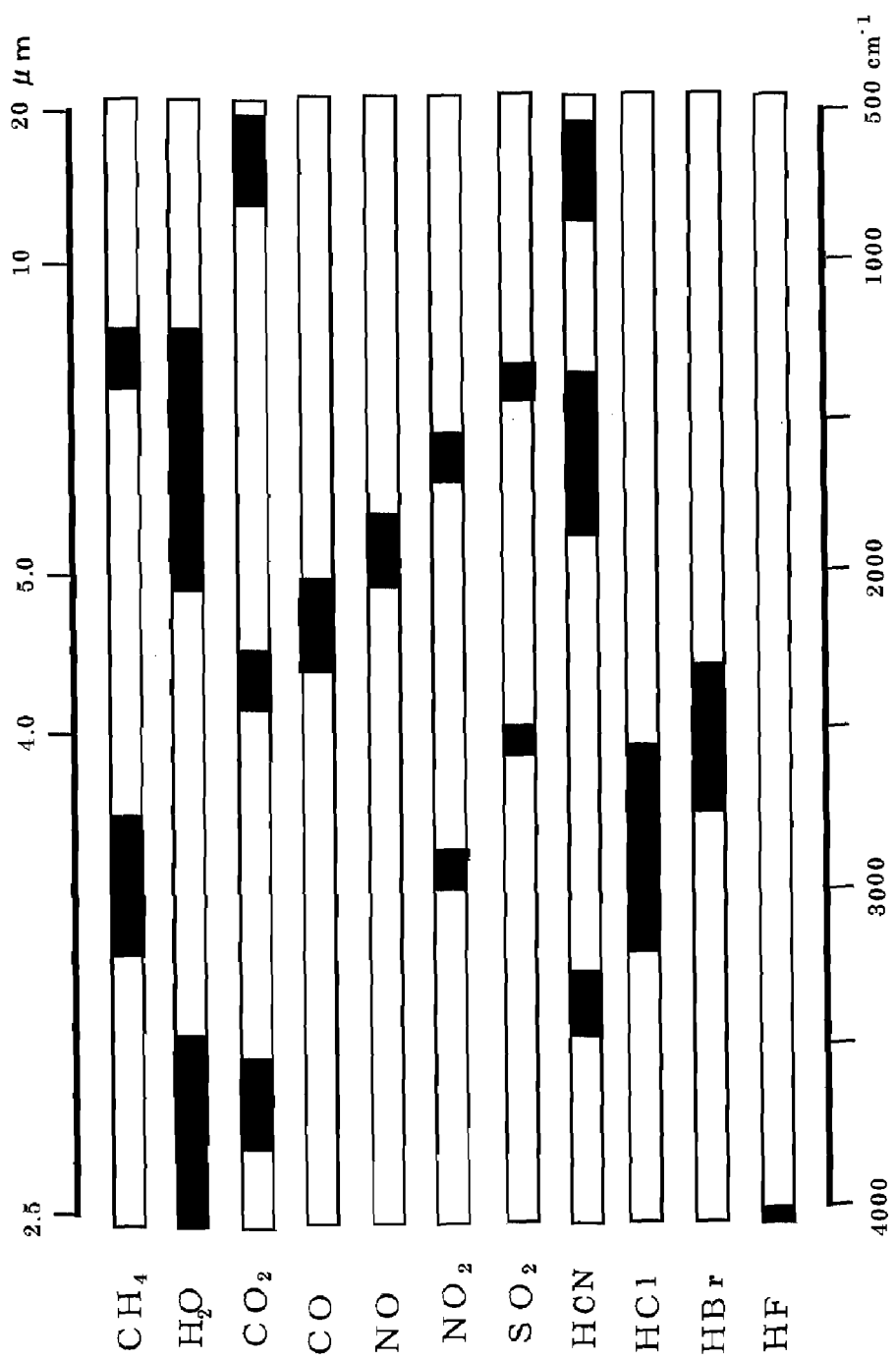
FIG. 2 is a chart illustrating infrared absorption bands of various gaseous substances.

FIG. 2 is a chart illustrating infrared absorption bands of various gaseous substances. In the chart, the abscissa axis on top represents the infrared wavelength, the abscissa axis at bottom represents the wave number corresponding to the wavelength and the areas darkened along the abscissa axes represent infrared absorption bands of the gaseous substances. From FIG. 2, it can be seen that the infrared absorption bands of NO and $NO_2$ range between 4.8 and 5.5 μm and between 5.9 and 6.3 μm, respectively.

Figure 3:
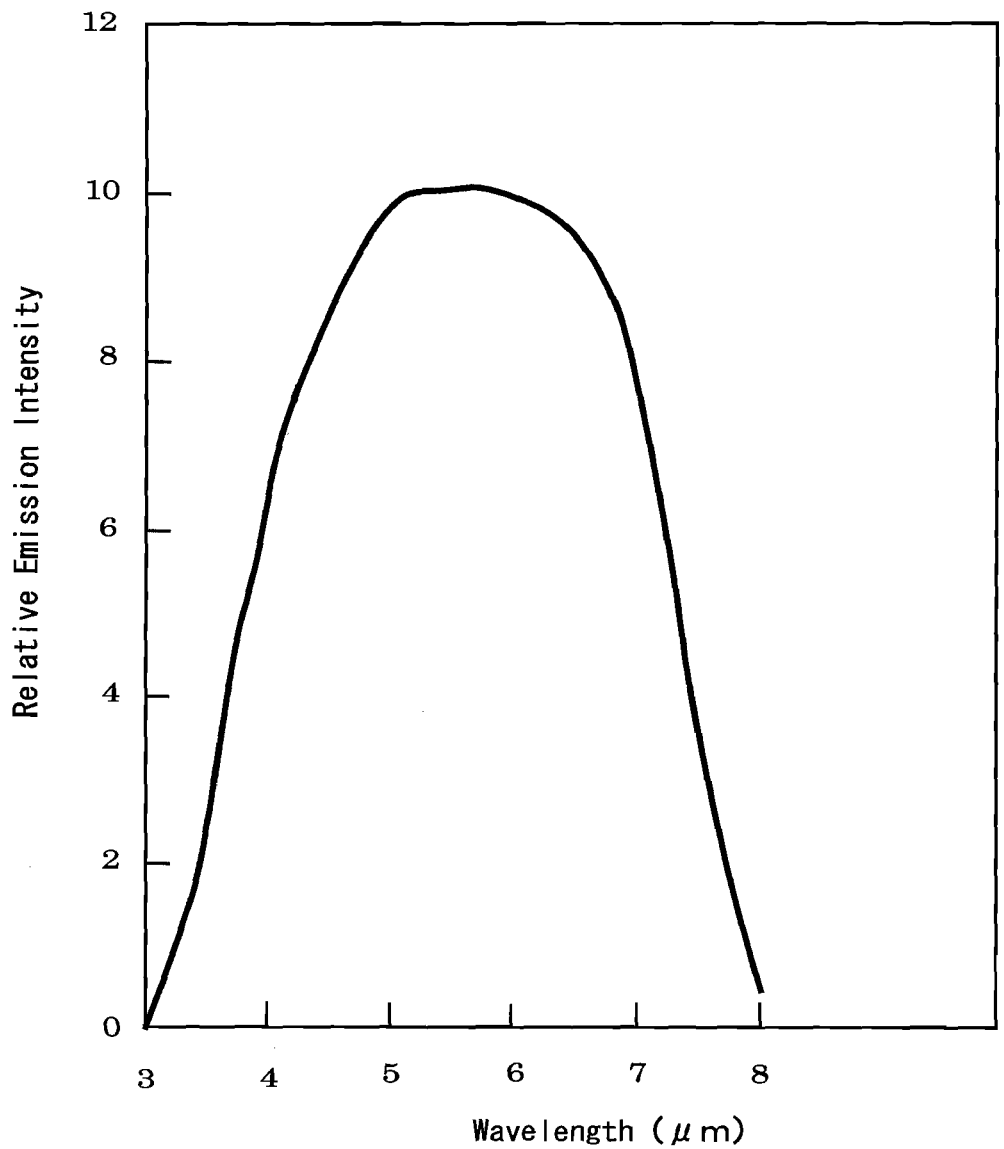
FIG. 3 is a graph illustrating an infrared light emitting band of InSb infrared light emitting diode.

FIG. 3 is a graph illustrating an infrared light emitting band of InSb infrared light emitting diode (made by Material Technologies, Inc.). From the graph, it is seen that this InSb infrared light emitting diode has an infrared light emitting band ranging between 3 to 6 μm, which is wider than and close to the infrared absorption bands of NO and $NO_2$.

Thus, if the analyte gases are NO and $NO_2$, it is then possible to use an InSb infrared light emitting diode as the infrared light emitting diode. Depending on types of a plurality of analyte gases to be measured, infrared light emitting diodes of various infrared light emitting bands are made available which are with different materials making up the infrared light emitting diodes, different impurities to be doped or different structures of the diodes. A suitable infrared light emitting diode can be selected according to particular types of a plurality of analyte gases to be measured.

A conventional infrared light source of thermal radiation type, e.g., a glow lamp, radiates emitted infrared light in all directions of 360°. For this reason, even if reflecting and collector mirrors are used, collimated infrared light of enough intensity could hardly be obtained and the infrared light intensity, namely, the collimated light intensity which could effectively be obtained in a conventional, portable measuring apparatus of this sort has been in the order of μW.

In contrast, an infrared light emitting diode which is of several tens of mW and if it is an infrared light emitting diode of surface emitting type has an angle of emission divergence of about 10° is available and can easily make its collimated light intensity about a hundred times higher than that of the conventional infrared light source of thermal radiation type. If the collimated light intensity is 100 times higher, it is then possible to increase the detection sensitivity 100 times higher by making the optical length of the multi-reflection sample gas cell 9 a hundred times longer.

The infrared light source may also be a broadband infrared semiconductor laser. The broadband infrared semiconductor laser is preferably a quantum cascade semiconductor laser (see, for example, Nonpatent References 2 and 3). The quantum cascade semiconductor laser utilizes infrared light emission by an inter-sublevel transition of a semiconductor quantum well and makes it possible to obtain a desired emission wavelength by adjusting the width of the quantum well. Thus, if a number of quantum wells of various well widths are connected in cascade, it is then possible to create a quantum cascade semiconductor laser having a desired infrared emission band in an infrared region from near infrared to far infrared. Using such an infrared light source makes it possible to detect a plurality of analyte gases ranging extremely widely in kind.

The broadband infrared semiconductor laser may be a IV-VI group semiconductor laser (see, for example, Nonpatent Reference 4). The IV-VI group semiconductor laser, which is small in Auger recombination probability and thus high in infrared emission efficiency, can be used as a broadband infrared semiconductor laser of mid- to far infrared region. The broadband infrared semiconductor laser may also be a III-V group semiconductor laser (see, e.g., Nonpatent Reference 5). The III-V group semiconductor laser can be used primarily as a broadband infrared semiconductor laser of mid-infrared region. A broadband infrared semiconductor laser is even higher in directivity than an infrared light emitting diode and can make the collimated light intensity still higher.

Since an infrared light source of thermal radiation type which generates a continuous spectrum over a broad range from near infrared to far infrared, it is difficult to completely cut off infrared light outside of a band over the near to far infrared range even if the band is limited by a bandpass filter. As a result, in the conventional apparatus such unnecessary infrared light becomes incident on the infrared detector, deteriorating the S/N ratio.

In contrast, an infrared light emitting diode or a broadband infrared semiconductor laser for use in an apparatus in accordance with the present invention has a minimum infrared emission band necessary for a measurement. Then, without a bandpass filter, infrared light arriving at the photodetector and unnecessary for measurement is extremely reduced and it is easy to make the S/N ratio of the photodetector around 100 times higher than with the light source of thermal radiation type.

Mention is next made of a further detail of the operation of the gas correlation filter in a gas concentration measuring apparatus according to the present invention. While in the following description two analyte gases in kind are illustrated as a plurality of analyte gases for simultaneous measurement, the operation is similar if they are three or more in kind.

Figure 4:
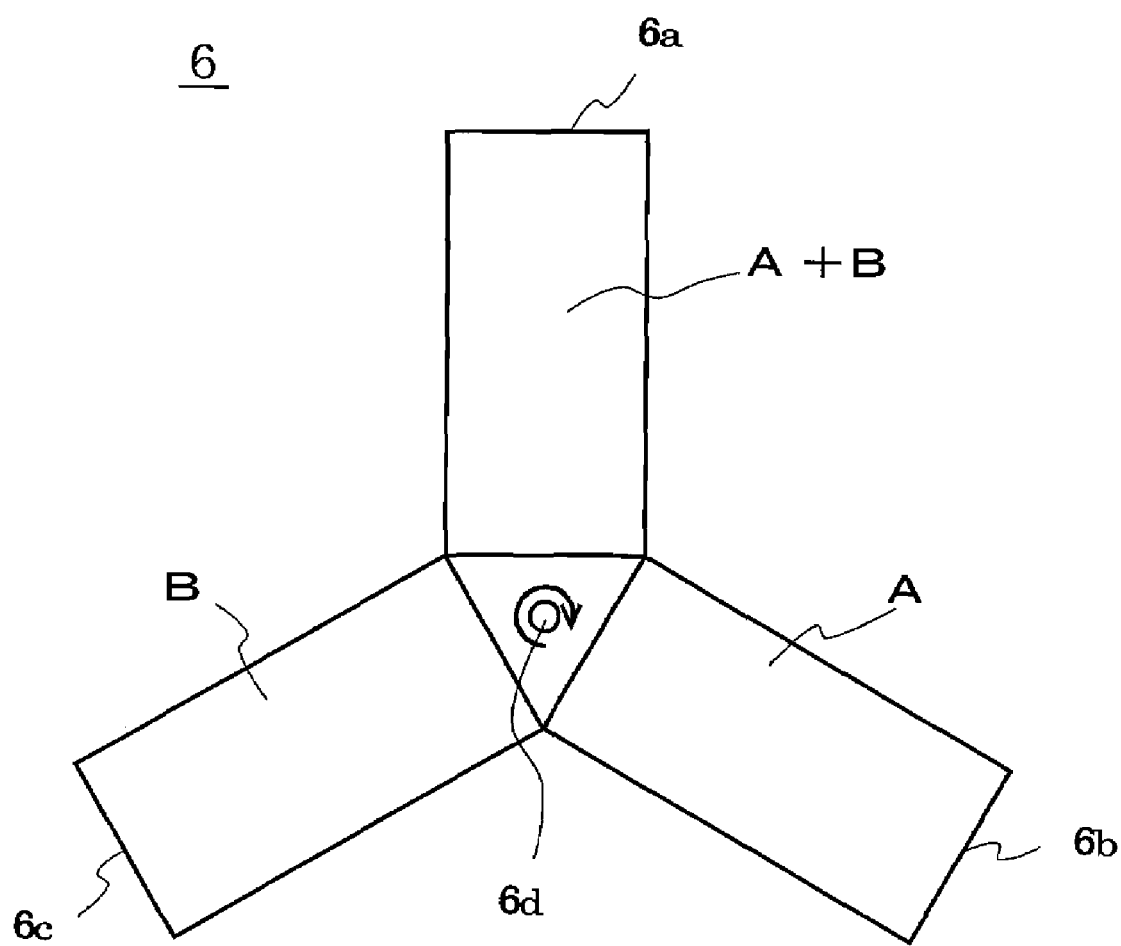
FIG. 4 is a view illustrating the makeup of a gas correlation filter in the apparatus of the present invention for gas concentration measurement according to the gas correlation method.

FIG. 4 shows the makeup of a gas correlation filter for use in an apparatus for measuring two different analyte gases simultaneously and is a front view thereof as viewed from the optical axis. The gas correlation filter 6 is made up of three gas cells 6a, 6b and 6c. Assuming that the two analyte gases are A and B, the gas cell 6a is filled with A and B gases, and the gas cells 6b and 6c are filled with A and B gases, respectively. Each gas cell is so loaded at a density such as to completely absorb the infrared absorption band or bands of the gas. The gas correlation filter 6 is rotated about the axis of rotation 6d to make infrared light 5 incident on the gas cells 6a, 6b and 6c successively.

Figure 5:
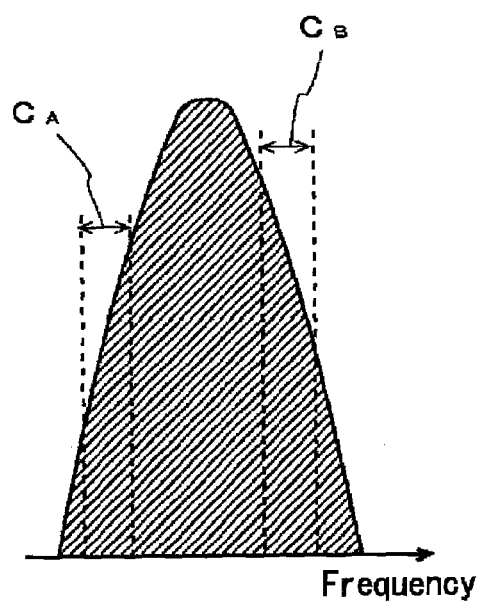
FIG. 5 carries charts illustrating an emission spectrum of an infrared light emission diode or a broadband infrared semiconductor laser as an infrared light source and spectra of infrared light passing through three gas cells, respectively, for use in the apparatus of the present invention.
Figure 5:
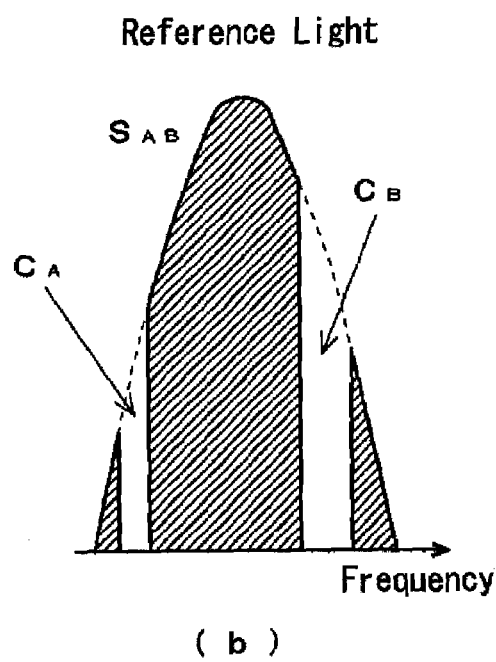
Figure 5:
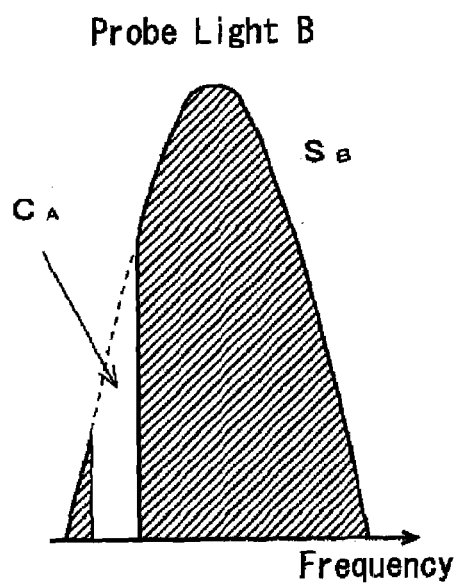
Figure 5:
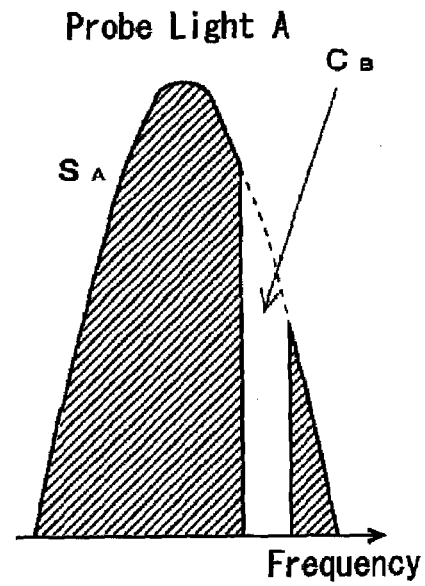

FIG. 5 carries charts illustrating an emission spectrum of an infrared light emission diode or a broadband infrared semiconductor laser as an infrared light source and spectra of infrared light passing through three gas cells, respectively, for use in this apparatus.

FIG. 5(*a*) shows the emission spectrum of infrared light 3. As is shown, a spectrum contains infrared absorption bands $C_A$ and $C_B$ of gases A and B and has a width close to these bands.

FIG. 5(*b*) shows a spectrum of transmitted infrared light when infrared light 3 is incident on and passes through the gas cell 6a filled with the A and B gases, the spectrum containing neither the infrared absorption band $C_A$ nor the infrared absorption band $C_B$. The transmitted light when incident on the multi-reflection sample gas cell 9 does not incur absorption by the analyte gases and is used as reference light for finding a loss of the multi-reflection sample gas cell 9, i.e. which is other than that due to absorption by the analyte gases. Spectral area $S_{AB}$ at the hatched portions in the chart is proportional to light intensity $I_{AB0}$ of the incident reference light.

FIG. 5(*c*) shows a spectrum of transmitted infrared light when infrared light 3 is incident on and passes through the gas cell 6b filled with the A gas. The shown spectrum does not contain the infrared absorption band $C_A$ of the A gas and contains the infrared absorption band $C_B$ of gas B is used as probe light B for gas B concentration measurement. Area $S_B$ at the hatched portion in the chart is proportional to light intensity $I_{B0}$ of incident probe light B.

FIG. 5(*d*) shows a spectrum of transmitted infrared light when infrared light 3 is incident on and passes through the gas cell 6c filled with the B gas. The shown spectrum does not contain the infrared absorption band $C_B$ of the B gas and contains the infrared absorption band $C_A$ of gas A is used as probe light A for gas A concentration measurement. Area $S_A$ at the hatched portion in the chart is proportional to light intensity $I_{A0}$ of incident probe light A.

As discussed in connection with the prior art, ratio in intensity $I_{B0}/I_{AB0}$ of incident probe light B and the incident reference light, which pass through the gas cells and are incident on the multi-refection sample gas cell, and ratio in intensity $I_{A0}/I_{AB0}$ of incident probe light A and the incident reference light are universal against changes in intensity of the output light 3 of the infrared light source 2 and changes in loss of the optical system due to contaminations of the collimator 4 and the gas correlation filter 6 and their deviations in optical axis and are measured in advance upon the manufacture of an apparatus.

Figure 6:
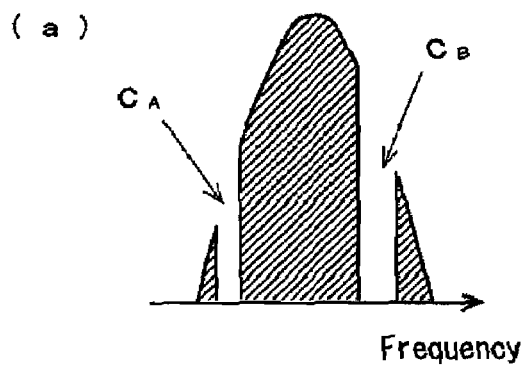
FIG. 6 carries charts illustrating spectra of reference light, probe light A and probe light B detected by an infrared detector.
Figure 6:
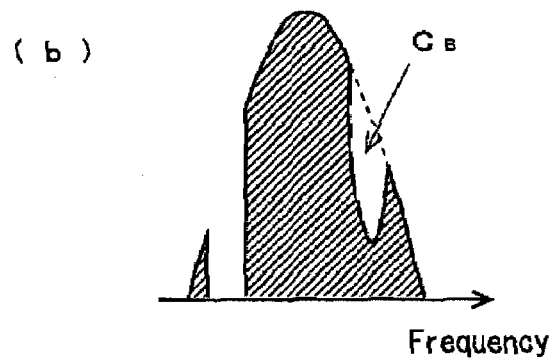
Figure 6:
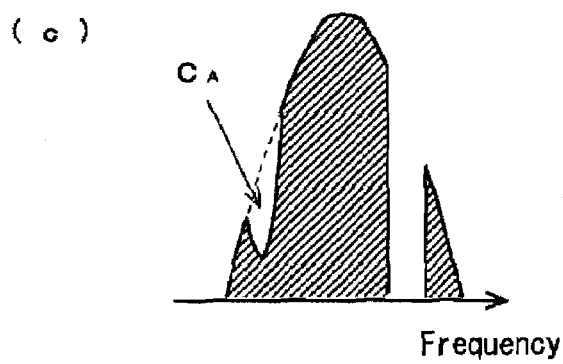

FIG. 6 carries charts illustrating spectra of reference light, probe light A and probe light B which are detected by the infrared detector 11.

FIG. 6(*a*) shows a spectrum of reference light passing through the multi-reflection sample gas cell 9 and detected by the infrared detector 11. The reference light detected at the infrared detector 11 is assumed to have intensity $I_{AB}$.

FIG. 6(*b*) shows a spectrum of probe light B passing through the multi-reflection sample gas cell 9 and detected by the infrared detector 11. As shown, at band portion $C_B$ absorption comes about according to a concentration of the analyte gas B in the multi-reflection sample gas cell. Since the probe light B does not have a spectral component corresponding to an infrared absorption band of the analyte gas A, it does not incur an absorption loss by the gas A and does incur loss γ other than the absorption loss by the analyte gas in the multi-reflection sample gas cell 9 and an absorption loss by the analyte gas B. Thus, assuming that the gas B has absorbance $α_B$, as discussed in connection with the prior art, equation (5) below is brought about between ratio $I_B/I_{AB}$ of probe light intensity $I_B$ and reference light intensity $I_{AB}$ which are detected by the infrared detector 11 and ratio $I_{B0}/I_{AB0}$ of incident probe light intensity $I_{B0}$ and incident reference light intensity $I_{AB0}$ which are measured in advance.

[Formula 5]

$$I_B/I_{AB}=(I_{B0}/I_{AB0})e^{-αB} \quad (5)$$

As discussed in connection with the prior art, the ratio $I_{B0}/I_{AB0}$ is constant against changes in intensity of the output infrared light 3 of the infrared light source 2 and changes in loss of the optical system of the collimator 4 and the gas correlation filter 6. The ratio $I_B/I_{AB}$ is constant against changes in loss other than the absorption loss by the analyte gas in the multi-reflection sample gas cell 9 and does not incur the absorption loss by the gas A in the multi-reflection sample gas cell 9. Therefore, from the absorbance $α_B$ found using the equation (5), the concentration of analyte gas B in a gas can be detected at high sensitivity without being affected by these loss changes and the concentration of gas A.

FIG. 6(*c*) shows a spectrum of probe light A passing through the multi-reflection sample gas cell 9 and detected by the infrared detector 11. As shown, at band portion $C_A$ absorption comes about according to a concentration of the analyte gas A in the multi-reflection sample gas cell. Since the probe light A does not have a spectral component corresponding to an infrared absorption band of the analyte gas B, it does not incur an absorption loss by the gas B and does incur loss γ other than the absorption loss by the analyte gas in the multi-reflection sample gas cell 9 and an absorption loss by the analyte gas A. Thus, assuming that the gas A has absorbance $α_A$, as discussed in connection with the prior art, equation (6) below is brought about between ratio $I_A/I_{AB}$ of probe light intensity $I_A$ and reference light intensity $I_{AB}$ which are detected by the infrared detector 11 and ratio $I_{A0}/I_{AB0}$ of incident probe light intensity $I_{A0}$ and incident reference light intensity $I_{AB0}$ which are measured in advance.

[Formula 6]

$$I_A/I_{AB}=(I_{A0}/I_{AB0})e^{-αA} \quad (6)$$

As discussed in connection with the prior art, the ratio $I_{A0}/I_{AB0}$ is constant against changes in intensity of the output light 3 of the infrared light source 2 and changes in loss of the optical system of the collimator 4 and the gas correlation filter 6. The ratio $I_A/I_{AB}$ is constant against changes in loss other than the absorption loss by the analyte gas in the multi-reflection sample gas cell 9 and does not incur the absorption loss by the gas B. Therefore, the concentration of analyte gas A in a gas can be detected from the absorbance $α_A$ found using the equation (6) at high sensitivity without being affected by these loss changes and the concentration of gas B.

While for the sake of clarity of the discussion, the analyte gases are assumed to be two in kind, if the analyte gases are three or more in kind, it will be obvious that the infrared light passing through the cell filled with all the analyte gases can be reference light and the infrared light passing through a particular gas cell filled with such all analyte gases other than particular one of the analyte gases which is of its particular interest to the particular gas cell can be probe light for the particular gas cell.

According to a second form of implementation of the present invention, there is provided an apparatus of the makeup which incorporates an infrared bandpass filter into the apparatus makeup mentioned above.

Figure 7:
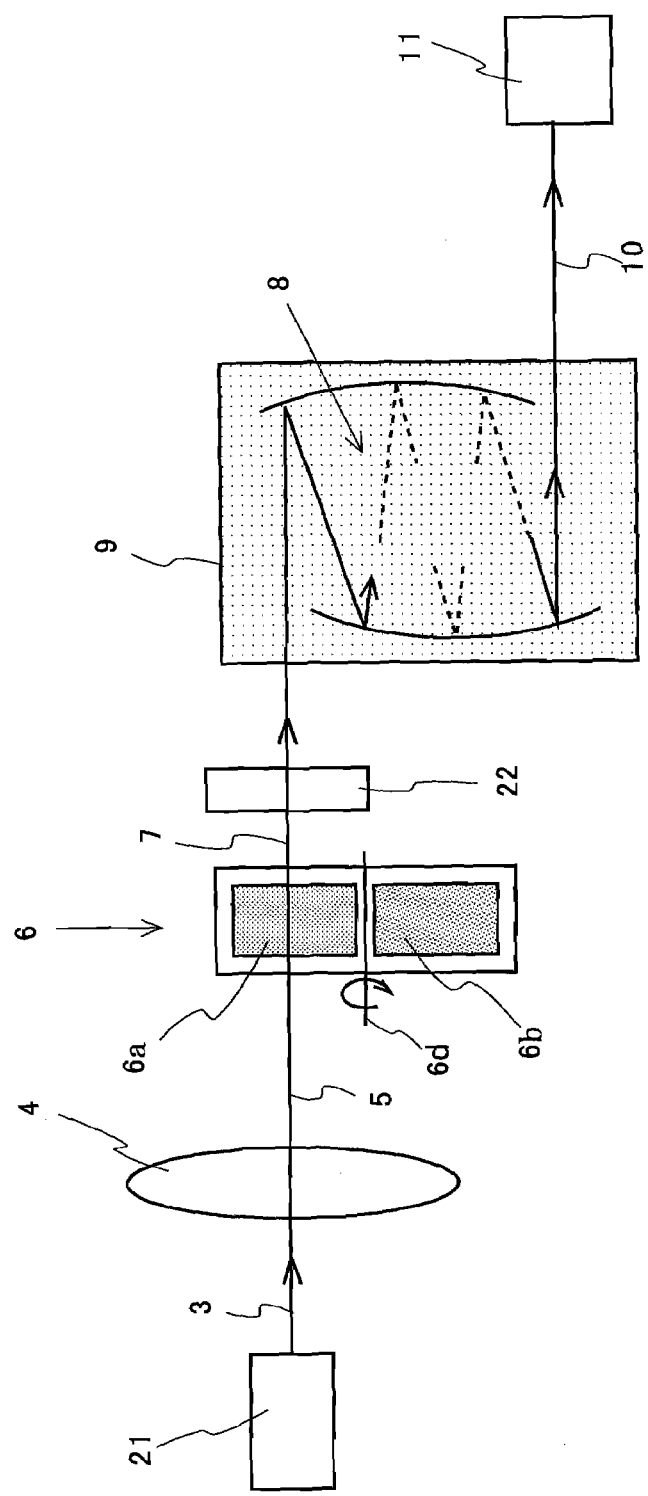
FIG. 7 is a diagram illustrating the makeup of an apparatus for gas concentration measurement according to a gas correlation method which represents a second best form of implementation of the present invention.

FIG. 7 is a diagram illustrating the makeup of an apparatus for gas concentration measurement according to a gas correlation method which represents the second best form of implementation of the present invention. This makeup differs from that of the first form of implementation described above in that the infrared light source has an emission band which contains, and which is close to but wider than, infrared absorption bands of a plurality of analyte gases. It also differs in that an infrared bandpass filter is included for forming the emission band of the infrared light source to be that which contains and is close to infrared emission bands of a plurality of analyte gases.

The first form of implementation has been described in which use is made of an infrared light source having an infrared emission band that contains and is close to infrared absorption bands of a plurality of analyte gases so that an infrared bandpass filter is unnecessary. In case such an infrared light source is unavailable, use may be made of an infrared light source having an infrared emission band wider than infrared absorption bands of a plurality of analyte gases together with an infrared bandpass filter 22 as shown so that its infrared emission band for use can be formed as that which contains and is close to infrared emission bands of a plurality of analyte gases.

INDUSTRIAL APPLICABILITY

As will be appreciated from the foregoing description, the present invention provides an apparatus for gas concentration measurement according to a gas correlation method in which use is made as the infrared light source of an infrared light emitting diode or a broadband infrared semiconductor laser to increase the infrared light intensity which can effectively be used and hence to increase the effective optical length. Without having unnecessary emissions which deteriorate the S/N ratio, such an infrared light source is high in detection sensitivity. A gas correlation filter used in the present apparatus comprises a reference gas cell filled with all of a plurality of analyte gases and a plurality of probe cells each individual of which is filled with all such analyte gases other than one of the analyte gases which is of its particular interest to the particular gas cell, which makes it possible to measure concentrations of such a plurality of analyte gases simultaneously.

Accordingly, the invention, e.g., when used as a simultaneous measuring apparatus for concentrations of air pollutants such as CO and NO in trace amounts in the field of terrestrial environment preserving technologies, is extremely useful.

What is claimed is:

1. An apparatus for gas concentration measurement according to a gas correlation method, characterized in that it comprises:
    an infrared light source made of an infrared light emitting diode;
    a collimator for collimating infrared light generated from the infrared light source;
    a gas correlation filter on which infrared light collimated by the collimator is incident;
    a multi-reflection sample gas cell on which infrared light passing through the gas correlation filter is incident and in which a gas to be measured containing a plurality of analyte gases is introduced or charged; and
    an infrared detector for detecting an intensity of infrared light passing through the multi-reflection sample gas cell, wherein:
    said infrared light source has an infrared light emission band wider than and close to infrared absorption bands of the analyte gases;
    said gas correlation filter comprises a reference gas cell and a plurality of probe gas cells corresponding in number to a plurality of said analyte gases;
    said reference gas cell and said probe gas cells are arranged so that the infrared light collimated as aforesaid passes successively through said reference gas cell and said probe gas cells, respectively; and
    said reference gas cell is filled with all of said analyte gases while each individual of said probe gas cells is filled with all such analyte gases other than one of said analyte gases which is of its particular interest,
    whereby concentrations of said analyte gases contained in said gas to be measured are measured at high sensitivity and simultaneously.

2. An apparatus for gas concentration measurement according to a gas correlation method, characterized in that it comprises:
    an infrared light source made of an infrared light emitting diode;
    a collimator for collimating infrared light generated from the infrared light source;
    a gas correlation filter on which infrared light collimated by the collimator is incident;
    a bandpass filter for limiting a band of infrared light passing through the gas correlation filter;
    a multi-reflection sample gas cell on which infrared light whose band is limited by the bandpass filter is incident and in which a gas to be measured containing a plurality of analyte gases is introduced or charged; and
    an infrared detector for detecting an intensity of infrared light passing through the multi-reflection sample gas cell, wherein:
    said infrared light source has an infrared light emission band wider than infrared absorption bands of said analyte gases;
    said gas correlation filter comprises a reference gas cell and a plurality of probe gas cells corresponding in number to a plurality of said analyte gases;
    said reference gas cell and said probe gas cells are arranged so that the infrared light collimated as aforesaid passes successively through said reference gas cell and said probe gas cells, respectively;
    said reference gas cell is filled with all of said analyte gases while each individual of said probe gas cells is filled with all such analyte gases other than one of said analyte gases which is of its particular interest, and
    said bandpass filter has a passband wider than and close to the infrared absorption bands of said analyte gases,
    whereby concentrations of said analyte gases contained in said gas to be measured are measured at high sensitivity and simultaneously.

3. An apparatus for gas concentration measurement according to a gas correlation method, characterized in that it comprises:
    an infrared light source made of a broadband infrared light emitting semiconductor laser;
    a collimator for collimating infrared light generated from the infrared light source;
    a gas correlation filter on which infrared light collimated by the collimator is incident;

a multi-reflection sample gas cell on which infrared light passing through the gas correlation filter is incident and in which a gas to be measured containing a plurality of analyte gases is introduced or charged; and an infrared detector for detecting an intensity of infrared light passing through the multi-reflection sample gas cell, wherein:

said infrared light source has an infrared light emission band wider than and close to infrared absorption bands of said analyte gases;

said gas correlation filter comprises a reference gas cell and a plurality of probe gas cells corresponding in number to a plurality of said analyte gases;

said reference gas cell and said probe gas cells are arranged so that the infrared light collimated as aforesaid passes successively through said reference gas cell and said probe gas cells, respectively; and said reference gas cell is filled with all of said analyte gases while each individual of said probe gas cells is filled with all such analyte gases other than one of said analyte gases which is of its particular interest, whereby concentrations of said analyte gases contained in said gas to be measured are measured at high sensitivity and simultaneously.

4. An apparatus for gas concentration measurement according to a gas correlation method, characterized in that it comprises:

an infrared light source made of a broadband infrared light emitting semiconductor laser;

a collimator for collimating infrared light generated from the infrared light source;

a gas correlation filter on which infrared light collimated by the collimator is incident;

a bandpass filter for limiting a band of infrared light passing through the gas correlation filter;

a multi-reflection sample gas cell on which infrared light whose band is limited by the bandpass filter is incident and in which a gas to be measured containing a plurality of analyte gases is introduced or charged; and an infrared detector for detecting an intensity of infrared light passing through the multi-reflection sample gas cell, wherein:

said infrared light source has an infrared light emission band wider than infrared absorption bands of said analyte gases;

said gas correlation filter comprises a reference gas cell and a plurality of probe gas cells corresponding in number to a plurality of said analyte gases;

said reference gas cell and said probe gas cells are arranged so that the infrared light collimated as aforesaid passes successively through said reference gas cell and said probe gas cells, respectively;

said reference gas cell is filled with all of said analyte gases while each individual of said probe gas cells is filled with all such analyte gases other than one of said analyte gases which is of its particular interest, and said bandpass filter has a passband wider than and close to the infrared absorption bands of said analyte gases, whereby concentrations of said analyte gases contained in said gas to be measured are measured at high sensitivity and simultaneously.

5. The apparatus for gas concentration measurement according to a gas correlation method as set forth in claim 3 or claim 4, characterized in that said broadband infrared light emitting semiconductor laser is a quantum cascade semiconductor laser having a number of quantum wells adjusted in well width and connected in cascade such that its emitted light has a band wider than and close to the infrared absorption bands of said analyte gases.

* * * * *